United States Patent
Peterson (10) Patent No.: US 8,043,275 B2
(45) Date of Patent: Oct. 25, 2011

(54) ABSORBENT GARMENT WITH DUAL CONTAINMENT FLAPS

(75) Inventor: Dale A. Peterson, Sayner, WI (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 1636 days.

(21) Appl. No.: 10/246,851

(22) Filed: Sep. 18, 2002

(65) Prior Publication Data

US 2003/0114827 A1    Jun. 19, 2003

Related U.S. Application Data (63) Continuation-in-part of application No. 10/024,954, filed on Dec. 19, 2001, now abandoned.

(51) Int. Cl.
*A61F 13/15* (2006.01)
*A61F 13/20* (2006.01)

(52) U.S. Cl. ......... 604/385.28; 604/385.25; 604/385.24; 604/385.26; 604/385.27

(58) Field of Classification Search ............. 604/385.01, 604/385.24–385.3, 392–396
See application file for complete search history.

(56) References Cited

U.S. PATENT DOCUMENTS

| | | | |
|---|---|---|---|
| 4,663,220 A | 5/1987 | Wisneski et al. | |
| 4,695,278 A | 9/1987 | Lawson | |
| 4,704,116 A | 11/1987 | Enloe | |
| 4,798,603 A | 1/1989 | Meyer et al. | |
| 4,808,177 A * | 2/1989 | DesMarais et al. | 604/385.27 |
| 4,816,025 A | 3/1989 | Foreman | |
| 5,021,051 A | 6/1991 | Hiuke | |
| 5,167,653 A | 12/1992 | Igaue et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,226,992 A | 7/1993 | Morman | |
| 5,304,159 A | 4/1994 | Tanji et al. | |
| 5,397,318 A | 3/1995 | Dreier | |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,527,302 A * | 6/1996 | Endres et al. | 604/385.21 |

(Continued)

FOREIGN PATENT DOCUMENTS

EP    0 217 032 A2    4/1987

(Continued)

OTHER PUBLICATIONS

Full translation of JP 2-152450.*

(Continued)

*Primary Examiner* — Tatyana Zalukaeva
*Assistant Examiner* — Susan Su
(74) *Attorney, Agent, or Firm* — Armstrong Teasdale LLP (57) ABSTRACT

An absorbent garment has a garment chassis, a pair of inner containment flaps and a pair of outer containment flaps. The inner and outer containment flaps are arranged on the garment chassis to inhibit leaking of body exudates from the garment during wear. In one embodiment, the inner containment flaps each have an elastic tension as determined by an elastic tension test which is substantially equal to an elastic tension of each outer containment flap as determined by the same test. In another embodiment, the inner containment flaps each have a height which is substantially equal to a height of each outer containment flap.

23 Claims, 4 Drawing Sheets

U.S. PATENT DOCUMENTS

| | | | |
|---|---|---|---|
| 5,540,796 | A | 7/1996 | Fries |
| H1630 | H | 1/1997 | Roe et al. |
| 5,595,618 | A | 1/1997 | Fries et al. |
| 5,601,544 | A | 2/1997 | Glaug et al. |
| 5,620,431 | A | 4/1997 | LeMahieu et al. |
| 5,669,896 | A | 9/1997 | Kielpikowski |
| 5,672,166 | A | 9/1997 | Vandemoortele |
| 5,674,215 | A | 10/1997 | Rönnberg |
| 5,695,868 | A | 12/1997 | McCormack |
| 5,746,732 | A | 5/1998 | Olsson et al. |
| 5,814,035 | A | 9/1998 | Gryskiewicz et al. |
| 5,814,036 | A | 9/1998 | Rönnberg et al. |
| 5,824,172 | A | 10/1998 | Kielpikowski |
| 5,843,056 | A | 12/1998 | Good et al. |
| 5,904,675 | A | 5/1999 | Laux et al. |
| 5,911,713 | A | 6/1999 | Yamada et al. |
| 5,913,851 | A | 6/1999 | Gryskiewicz et al. |
| 5,993,433 | A | 11/1999 | St. Louis et al. |
| 6,110,158 | A | 8/2000 | Kielpikowski |
| 6,121,510 | A | 9/2000 | Sauer |
| 6,149,934 | A | 11/2000 | Krzysik et al. |
| 6,186,996 | B1 | 2/2001 | Martin |
| 6,293,934 | B1 | 9/2001 | Kumasaka |
| 6,328,724 | B1 | 12/2001 | Ronnberg et al. |
| 6,383,170 | B1 | 5/2002 | Mishima et al. |
| 6,440,117 | B1 | 8/2002 | Itoh et al. |
| 6,451,001 | B2 | 9/2002 | Kumasaka |
| 6,648,869 | B1 * | 11/2003 | Gillies et al. ............. 604/385.28 |
| 6,699,228 | B1 * | 3/2004 | Chmielewski et al. .. 604/385.28 |
| 2002/0151861 | A1 * | 10/2002 | Klemp et al. ............ 604/385.19 |
| 2003/0073974 | A1 * | 4/2003 | Falconer ....................... 604/514 |
| 2003/0078557 | A1 * | 4/2003 | Vergona |

FOREIGN PATENT DOCUMENTS

| | | |
|---|---|---|
| EP | 0 386 815 A3 | 12/1990 |
| EP | 0 346 477 B1 | 12/1992 |
| EP | 0 913 137 A2 | 6/1999 |
| EP | 1055403 A2 * | 11/2000 |
| EP | 1 106 152 A1 | 6/2001 |
| GB | 2 193 625 A | 2/1988 |
| JP | 02-65860 | 3/1990 |
| JP | 2-71521 * | 5/1990 |
| JP | 02-152450 | 6/1990 |
| JP | 02-174845 | 7/1990 |
| JP | 3-218752 * | 9/1991 |
| JP | 03-218752 | 9/1991 |
| JP | 4-99921 * | 8/1992 |
| JP | 10179638 A * | 7/1998 |
| JP | 10277092 A * | 10/1998 |
| JP | 2000079141 | 3/2000 |
| JP | 02001087307 A * | 4/2001 |
| WO | WO 96/26698 A1 | 9/1996 |
| WO | WO 9829074 A1 * | 7/1998 |
| WO | WO 98/37838 | 9/1998 |

OTHER PUBLICATIONS

Full translation of JP 2-174845.*
Derwent abstract for 1997-191022-KR 9508172 B1-2 pgs.*
International Search Report for PCT/US 02/37012 dated Nov. 18, 2002, 5 pages.
Ultra Moony Diaper Disclosure Statement, dated Jun. 4, 2003, 1 page.

* cited by examiner

FIG. 6

ABSORBENT GARMENT WITH DUAL CONTAINMENT FLAPS

FIELD OF THE INVENTION

The present invention relates to absorbent garments. More specifically, the present invention relates to disposable absorbent garments, such as diapers and adult incontinence garments, comprising dual containment flaps.

BACKGROUND OF THE INVENTION

Absorbent garments such as disposable diapers, training pants, adult incontinent garments, and the like, are well known. Such absorbent garments employ an absorbent body between an outer cover and a bodyside liner. In order to improve the ability of absorbent garments to absorb and reduce leakage of discharged body wastes, it has become common to include elastic waistbands and leg cuffs on such garments. Some conventional absorbent garments have also included elastic barrier flaps at the leg sections to further reduce leakage.

Conventional absorbent garments that include containment flaps have not been completely satisfactory. Conventional flaps in such garments include a single flap at each side of the garment. Each single flap includes a proximal edge attached to the garment and an elasticized distal edge opposite the proximal edge. The single containment flap is attached to the garment such that the distal edge of the containment flap is maintained in a generally upright position to contact the body of a wearer, thereby providing a seal that attempts to prevent the flow of bodily exudate. However, a single containment flap often fails to provide an adequate seal between the distal edge of the flap and the wearer's body. The lack of an adequate seal results in leakage of exudates and, in particular, runny fecal matter. Moreover, the single containment flap often fails and is particularly ineffective against forceful and repetitive expelling of exudates. The leakage of exudates past the containment flap results in soiling the clothing, bedding, and person. Obviously, this is undesirable.

Examples of containment flaps are taught in U.S. Pat. No. 4,704,116 (hereby incorporated by reference) and U.S. Pat. No. 6,110,158 (hereby incorporated by reference). Garments having two containment flaps on each side of the garment are also known. For example, some garments have an inner pair of containment flaps and an outer pair of containment flaps with the inner flaps positioned closer to the center of the garment than the outer flaps. Some garments have elastic members along the distal edge of a containment flap to provide a closer fit to the wearer. However, conventional elastic members are provided at such a high elastic tension or high elongation that the wearer's skin is irritated or marked by the flap/elastic member assembly.

One multiple flap construction is described in U.S. Pat. No. 5,167,653. This patent generally describes a disposable garment for catching body fluids or excretions and particularly to a garment provided with a plurality of flaps extending longitudinally side-by-side along laterally opposite sides of the garment and normally biased by their own elastic shrinking potential to turn up.

WO 96/26698, which corresponds to U.S. application Ser. No. 08/396,949, describes a disposable absorbent article such as a diaper. The diaper has dual upstanding inner and outer barrier leg cuffs, and preferably gasket cuffs. The inner barrier leg cuffs are liquid pervious, while the outer barrier leg cuffs are liquid impermeable. The inner barrier leg cuffs are preferably spaced apart from one another sufficient to allow urine and fecal material to be deposited therebetween. Each outer barrier leg cuff is preferably spaced properly from the inner barrier leg cuff so as to allow the leg cuffs to function independently, yet maintain a proper target area for the deposition of urine and fecal material.

Ovisan-Kimberly of Istanbul, Turkey, manufactures a diaper under the trade name PEDO DUO that has a dual flap construction including inner and outer containment flaps on each of the left and right sides of the diaper. As determined by an Elastic Tension Test described later herein, the outer containment flap of the Ovisan-Kimberly diaper has an elastic tension which is at least fifteen percent greater than the elastic tension in the inner containment flap. The height of each inner containment flap, as measured from the liner to the distal edge of the flap at the longitudinal center thereof is approximately 25 mm. The height of each outer containment flap is approximately 29 mm and is in any event at least about fifteen percent greater than the height of the inner flaps. The elasticized lengths of the inner and outer containment flaps of the PEDO DUO diaper are substantially equal and are approximately 80 percent of the overall length of the diaper.

Conventional absorbent garments with containment flaps at the leg openings have not been completely satisfactory. Accordingly, a need remains to improve containment at the leg openings of absorbent garments.

SUMMARY OF THE INVENTION

In response to the difficulties and problems discussed herein, a new disposable absorbent garment is presented herein. Specifically, the present invention provides improved absorbent garments having dual containment flaps. It has been discovered that absorbent garments comprising dual containment flaps have reduced leakage if the inner containment flaps and outer containment flaps have substantially equal elastic tensions. Further, the elastic tension of the containment flaps according to the present invention provides a seal to reduce leakage, yet still provides a comfortable fit with reduced opportunity for causing skin marking and irritation. It has also been discovered that absorbent garments comprising dual containment flaps exhibit reduced leakage if the inner containment flaps and outer containment flaps have substantially equal height.

In general, an absorbent garment of one embodiment of the present invention comprises a garment chassis, a pair of inner containment flaps and a pair of outer containment flaps. The inner and outer containment flaps are arranged on the garment chassis to inhibit leaking of body exudates from the garment during wear. The inner containment flaps each have an elastic tension as determined by an Elastic Tension Test which is substantially equal to within at least about 10 percent of an elastic tension of each outer containment flap as determined by the Elastic Tension Test.

In another embodiment the absorbent garment generally comprises a garment chassis, a pair of inner containment flaps and a pair of outer containment flaps. The inner and outer containment flaps are arranged on the garment chassis to inhibit leaking of body exudates from the garment during wear. The inner containment flaps each have a height which is substantially equal to within at least about 10 percent of a height of each outer containment flap.

DESCRIPTION OF THE DRAWINGS

The present invention is illustrated by way of example in the following drawings in which like references indicate similar elements. The following drawings disclose various embodiments of the present invention for purposes of illustration only and are not intended to limit the scope of the invention.

DEFINITIONS

As used herein the terms "attached" and "bonded" both refer to joining, adhering, connecting, or the like of elements. The elements are considered to be bonded and/or attached together when they are bonded directly to each other or indirectly through intermediate elements to each other. This definition also applies to words of similar meaning.

As used herein, the term "comprise" and its derivatives are intended to be open ended terms that specify the presence of the stated features, elements, components, groups, integers, and/or steps, but do not exclude the presence of other, unstated features, elements, components, groups, integers, and/or steps. This definition also applies to words of similar meaning, for example, the terms "has" and "include" and their derivatives.

As used herein, the terms "elastic" and "elastomeric" and their derivatives refer to a property of a material by virtue of which the material tends to recover its original size and shape after removal of a force causing the material to deform.

As used herein, the term "layer" when used in a singular form may refer to a single unitary element or a plurality of elements.

As used herein, the term "nonwoven" refers to an element formed without weaving or knitting.

As used herein, the term "hydrophilic" refers to fibers or surfaces of fibers that are wetted by an aqueous liquids in contact with the fibers. The degree of wetting materials can, in turn, be described in terms of contact angles and the surface tensions of liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated as wettable or hydrophilic, while fibers having contact angles of greater than 90 degrees are designated as nonwettable or hydrophobic.

As used herein, the term "machine direction" or MD means the length of a material or fabric in the direction in which it is produced. The term "cross-machine direction" or CD means the width of a material or fabric, i.e., a direction generally perpendicular to the MD.

DETAILED DESCRIPTION OF THE INVENTION

In the following detailed description of the present invention, reference is made to the accompanying drawings, which form a part hereof, and in which are shown by way of illustration specific embodiments in which the present invention may be practiced. It should be understood that other embodiments may be utilized and structural changes may be made without departing from the scope of the present invention.

Figure 1:
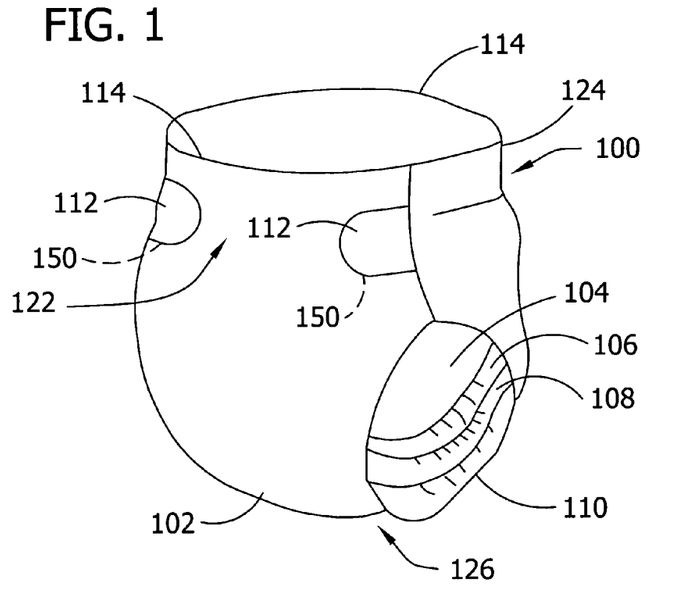
FIG. 1 is a side perspective view illustrating an individual disposable diaper of the present invention in a fastened position.
Figure 2:
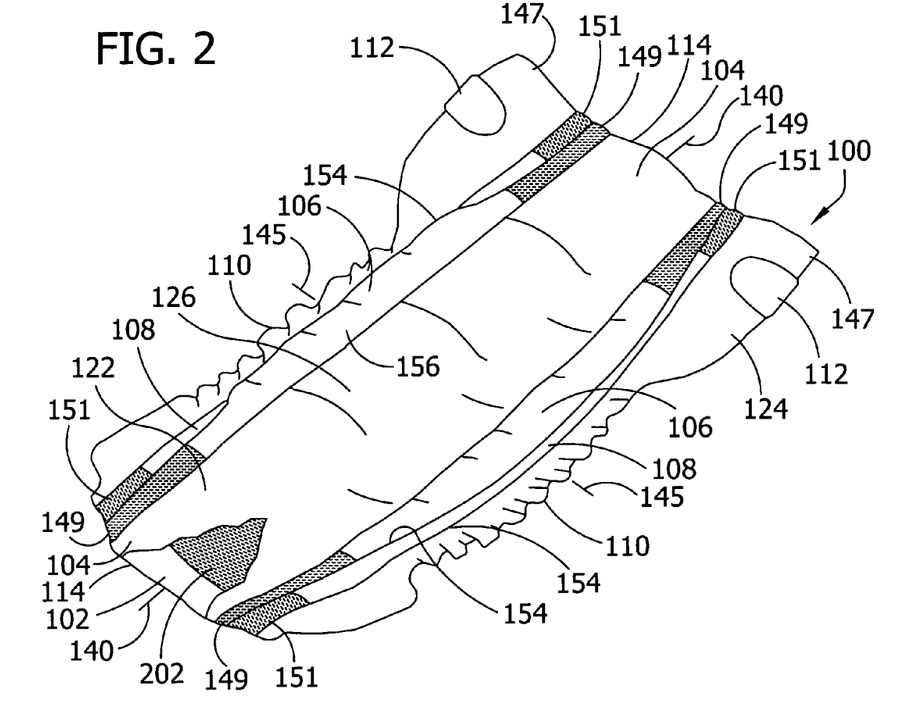
FIG. 2 illustrates the diaper of FIG. 1 in a flat state showing the side that faces a wearer when worn and with a bodyside liner partially broken away to reveal internal construction.

The present invention provides for absorbent garments that exhibit reduced leakage. Garments of the present invention comprise dual containment flaps. FIGS. 1 and 2 illustrate an example of a disposable garment, such as diaper 100, made in accordance with the present invention. FIG. 1 shows the diaper 100 in its folded, wearable position. Diaper 100 comprises a garment chassis that includes an outer cover 102, a bodyside liner 104, and an absorbent layer 202. Diaper 100 further comprises a pair of fasteners 112, a pair of inner containment flaps 106 attached to the garment chassis, and a pair of outer containment flaps 108 attached to the garment chassis. In an embodiment, the pair of inner containment flaps 106 is attached to bodyside liner 104. In an embodiment, the pair of outer containment flaps 108 is attached to bodyside liner 104.

FIG. 2 illustrates diaper 100 in an unfastened, stretched, and laid flat configuration with the bodyside liner 104 facing the viewer and with a portion of the diaper partially cut away to show the underlying features. The illustrated diaper 100 includes a first waistband portion, such as front waistband portion 122, and a second waistband portion, such as back waistband portion 124. An intermediate portion, such as crotch portion 126, interconnects the front waistband portion 122 to the back waistband portion 124. Diaper 100 has a longitudinal center line 140, a lateral center axis 145 extending generally perpendicular to the center line 140. In use, the diaper 100 is folded generally at lateral axis 145 such that the front portion 122 abuts the lower front torso of the wearer, the rear portion 124 abuts the lower rear torso of the wearer, and the crotch portion extends from the front portion 122 to the rear portion 124 through the crotch of the wearer.

Fasteners 112 include hook and loop type fasteners. Other types of fasteners including adhesive tape, buttons, pins, snaps, cohesives, mushroom and loop fasteners and the like, may be employed to fasten the portions 122 and 124 together. In an embodiment, the diaper 100 includes side panels 147 onto which the fasteners are fixed. One side panel 147 is fixed on each of the side of rear portion 124. It will be appreciated that the side panels 147 could be attached to the front portion 122. The side panels 147 may be elastic or otherwise rendered elastomeric. For example, the side panels 147 may be an elastomeric material such as a neck-bonded laminate "NBL" or stretch-bonded laminate "SBL" material. Methods of making such materials are described in U.S. Pat. Nos. 4,663,220 and 5,226,992, and EP Patent Application No. 0 217 032, the disclosures of which are hereby incorporated by reference. Examples of articles or garments that include elasticized side panels and selectively configured fasteners are described in U.S. Pat. Nos. 5,496,298; 5,540,796; and 5,595,618; the disclosures of which are hereby incorporated by reference.

In a desirable embodiment, the fasteners 112 are hook type fasteners that are connectable and releasable to the front waistband portion 122. Such a fastener 112 provides the ability to vary the size of the waist opening defined by the diaper 100 in small increments over a wide range of wearer waist sizes. The front waistband portion 122, in an embodiment, includes a landing zone 150 positioned on an outer surface of the outer cover 102. Landing zone 150 is adapted to releasably receive the fastener 112 to join the front and rear portions of the diaper 100.

The bodyside liner 104 is connected to the outer cover 102 in a superposed relation. An absorbent core 202 is located between the outer cover 102 and the bodyside liner 104. The laterally opposed side edges 110 of the diaper 100 are generally defined by the side edges of the outer cover 102. The side edges 110 define leg openings that may be curvilinear. The waist edges 114 of the diaper 100 are generally defined by the waist edges of the outer cover 102 and define a waist opening, which is configured to encircle the waist of the wearer when the diaper 100 is worn. FIG. 2 further illustrates a pair of inner containment flaps 106 and a pair of outer containment flaps 108.

The diaper 100 may be of various suitable shapes. For example, in the unfastened configuration as illustrated in FIG. 2, the diaper may have an overall generally rectangular shape, T-shape, or a generally I-shape. In the embodiment shown in FIG. 2, diaper 100 has an approximately hourglass shape in an unfastened configuration. Examples of diaper configurations suitable for use in connection with the instant application and other diaper components suitable for use on diapers in accordance with the present invention are described in U.S. Pat. No. 4,798,603; U.S. Pat. No. 5,176,668; U.S. Pat. No. 5,176,672; U.S. Pat. No. 5,192,606; U.S. Pat. No. 5,509,915; and U.S. Pat. No. 6,121,510; the teachings of which are all herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 100 are integrally assembled together employing various types of suitable attachment means, such as adhesive, sonic and thermal bonds or combinations thereof. For example, the outer cover 102 and the bodyside liner 104 may be assembled to each other and to the absorbent core 202 with adhesive, such as a hot melt adhesive or a pressure-sensitive adhesive, to form the garment chassis. The adhesive may be applied as a uniform continuous layer of adhesive, a patterned layer of adhesive, a sprayed pattern of adhesive, or an array of separate lines, swirls or dots of adhesive. Alternately, the absorbent core 202 may be connected to the outer cover 102 using conventional fasteners such as buttons, hook and loop type fasteners, adhesive tape fasteners, and the like. The other components of the diaper 100 may be suitably connected together using similar means. Similarly, other diaper components, such as the fasteners 112, may be assembled into the diaper 100 article by employing the above-identified attachment mechanisms and methods. Desirably, the majority of the diaper components are assembled together using ultrasonic bonding techniques for reduced manufacturing cost. These techniques are used, in an embodiment, to connect the containment flaps 106, 108 to the garment chassis at attachment zones 149, 151.

The outer cover 102 of the diaper 100, as representatively illustrated in FIG. 2, may suitably be composed of a material that is either liquid permeable or a material that is liquid impermeable. It is generally preferred that the outer cover 102 be formed from a material that is substantially impermeable to liquids. Materials useful in making such a liquid-impermeable outer cover include those known in the art. A typical outer cover can be manufactured from a thin plastic film or other flexible liquid-impermeable material. For example, the outer cover 102 may be formed from a polyethylene film having a thickness of from about 0.013 millimeter (0.5 mil) to about 0.051 millimeter (2.0 mils). If it is desired to present the outer cover 102 with a more cloth-like feel, the outer cover 102 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers of about 1.5 to 2.5 denier per filament. The nonwoven web has a basis weight of about 17 grams per square meter (0.5 ounce per square yard). The outer cover 102 may otherwise include bicomponent fibers, such as polyethylene/polypropylene bicomponent fibers. Methods of forming such cloth-like outer covers are known to those skilled in the art.

Further, the outer cover 102 may be formed of a woven or nonwoven fibrous web layer that has been totally or partially constructed or treated to impart a desired level of liquid impermeability to selected regions that are adjacent or proximate the absorbent core 202. Still further, the outer cover 102 may optionally be composed of a micro-porous "breathable" material that permits vapors to escape from the absorbent core 202 while still preventing liquid exudates from passing through the outer cover 102. For example, the outer cover 102 may include a vapor permeable non-woven facing layer laminated to a micro-porous film. Suitable "breathable" outer cover materials are described in U.S. Pat. No. 5,695,868 and U.S. Pat. No. 5,843,056, the teachings of which are both hereby incorporated by reference. Still further, the outer cover 102 may also be an elastomeric material, such as a stretch-thermal laminate ("STL"), neck-bonded laminate ("NBL"), or stretch-bonded laminate ("SBL") material. Methods of making such materials are well known to those skilled in the art and are described in U.S. Pat. No. 4,663,220; U.S. Pat. No. 5,226,992; and European Pat. Application No. EP 0 217 032; the teachings of which are all hereby incorporated by reference. The outer cover 102 can also be embossed or otherwise provided with a matte finish to provide a more aesthetically pleasing appearance.

Bodyside liners or garment inner covers, as representatively illustrated in FIG. 2 as bodyside liner 104, are adapted to contact the wearer's skin. That is, when worn, the bodyside liner of the absorbent garment faces the wearer and the outer cover faces away from the wearer. Accordingly, the side of a disposable diaper comprising the bodyside liner is commonly referred to as the bodyside or inner side of the garment. The bodyside liner is suitably employed to help isolate the wearer's skin from liquids held in the absorbent core 202. Thus, bodyside liners suitably present a bodyfacing surface that is compliant, soft feeling, and nonirritating to the wearer's skin. Further, bodyside liners may be less hydrophilic than the absorbent core, to present a relatively dry surface to the wearer, and may be sufficiently porous to be liquid permeable, permitting liquid to readily penetrate through is thickness. A suitable bodyside liner may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

Various woven and nonwoven fabrics can be used for the bodyside liners in accordance with the present invention. For example, the bodyside liners may be composed of a meltblown or spunbonded web of polyolefin fibers. Bodyside liners may also be a bonded-carded web composed of natural and/or synthetic fibers. Bodyside liners may be composed of a substantially hydrophobic material, and the hydrophobic material may optionally be treated with a surfactant or otherwise processed to impart a desired level of wettability and hydrophilicity. In one embodiment of the present invention, the bodyside liner comprises a nonwoven, spunbond, polypropylene fabric composed of about 2.8-3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemical, Inc. under the trade designation AHCOVEL Base N-62. The surfactant may be applied by any conventional means, such as spraying, printing, brush coating or the like. The surfactant may be applied to the entire bodyside liner or may be selectively applied to particular sections of the bodyside liner, such as the medial section along the longitudinal centerline of the diaper, to provide greater wettability of such sections. Bodyside liners may further include a composition applied thereto that is configured to be transferred to the wearer's skin for improving the skin health of the wearer. Suitable compositions for use on the bodyside liner are described in U.S. Pat. No. 6,149,934 (hereby incorporated by reference).

Absorbent cores, such as absorbent core 202 representatively illustrated in FIG. 2, may suitably include a matrix of hydrophilic fibers, such as a web of cellulosic fluff, mixed with particles of a high-absorbency material commonly known as superabsorbent material. In a particular aspect, the absorbent core includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent core to better contain and absorb body exudates. The concentration of the superabsorbent particles may also vary through the thickness of the absorbent core. Alternatively, the absorbent core may include a laminate of fibrous webs and superabsorbent material or other suitable means of maintaining a superabsorbent material in a localized area.

The absorbent core 202 may have any of a number of shapes. For example, the absorbent core may be rectangular, I-shaped, or T-shaped. It is generally preferred that the absorbent core be narrow in the crotch region 126 of the diaper 100. It has been found that the absorbent core of the present invention is particularly useful when the width dimension in the crotch region is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent core 202 allows the absorbent core to better fit between the legs of the wearer. The size and the absorbent capacity of the absorbent core should be compatible with the size of the intended wearer and the liquid loading imparted by the intended use of the absorbent article.

Materials useful in making absorptive cores in accordance with the present invention can be those known in the art. Useful high-absorbency materials can be selected from natural, synthetic, and modified natural polymers and materials. High-absorbance materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such a hydrolyzed acrylonitrile-grafted starch, acrylic acid grafted star, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM3900 polymer available from Hoechst Celanese, DOW DRYTECH 2035LD polymer available from The Dow Chemical Company, and Stockhausen W65431 polymer available from Stockhausen Inc.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. As a general rule, the high-absorbency material is present in the absorbent core in an amount of from about 5 to about 90 weight percent based on total weight of the absorbent core.

The diaper 100, in an embodiment, includes a ventilation layer (not shown) located between the absorbent body 202 and outer cover 102. The ventilation layer insulates the outer cover 102 from the absorbent body 202 to reduce the dampness of the outwardly facing, clothes contacting outer cover 102.

Diaper 100 can also include a surge management layer (not shown) which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, a surge layer can be located on an inwardly facing body side surface of inner layer 104. Alternatively, surge layer may be located adjacent to an outer side surface of inner layer 104. Accordingly, the surge layer would then be interposed between inner layer 104 and absorbent body 202. Examples of suitable surge management layers are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996, and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996, the entire disclosures of which are hereby incorporated by reference in a manner that is consistent herewith.

Optionally, a substantially hydrophilic tissue wrapsheet (not illustrated) may be employed to help maintain the integrity of the airlaid fibrous structure of the absorbent core. The tissue wrapsheet is typically placed about the absorbent core over at least the two major facing surfaces thereof and composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers comprising the absorbent core. The wrapsheet material on one side of the absorbent fibrous mass may be bonded to the wrapsheet located on the opposite side of the fibrous mass to effectively entrap the absorbent core.

Figure 5:
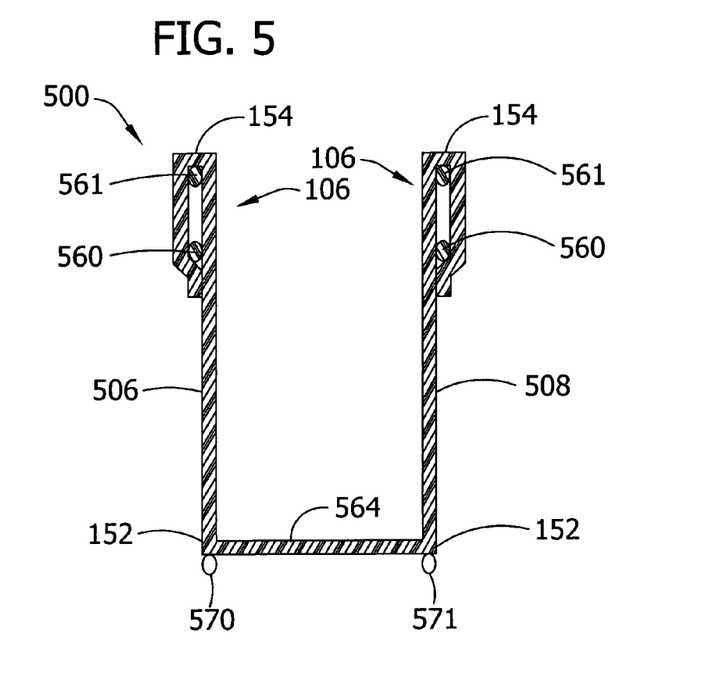
FIG. 5 is a cross-sectional view of single-layer dual containment flaps according to the present invention.
Figure 6:
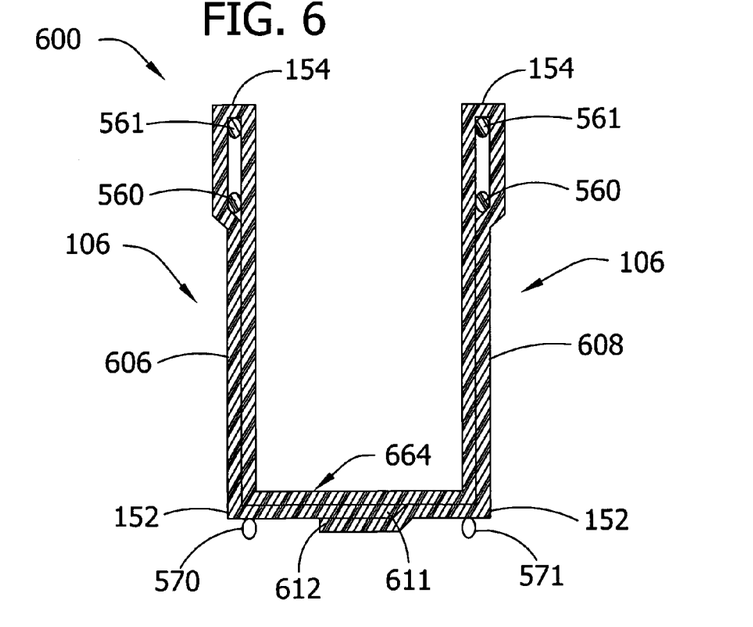
FIG. 6 is a cross-sectional view of double-layer dual containment flaps according to the present invention.

An absorbent garment according to the present invention, such as diaper 100 in FIG. 1, also comprises a pair of longitudinally extending inner containment flaps 106 and a pair of longitudinally extending outer containment flaps 108. The containment flaps are configured to provide a barrier to the lateral flow of body exudates. In an embodiment, the flaps 106, 108 are adapted to prevent flow of body exudates out the leg holes as shown in FIG. 1. As shown in FIGS. 2, 5 and 6, containment flaps 106, 108 according to the present invention are typically positioned substantially parallel to each other with the outer containment flaps 108 positioned closer to the outer edge of the garment and the inner containment flaps 106 positioned further away from the outer edge of the garment. The containment flaps may extend longitudinally along the entire length of the absorbent core 202 or may only extend partially along the length of the absorbent core. When the containment flaps are shorter in length than the absorbent core, the containment flaps can be selectively positioned anywhere along the side edges 110 of the diaper 100. In one embodiment of the present invention, the containment flaps 106, 108 extend along the entire length of the absorbent core to better contain the body exudates. In one embodiment of the present invention, the containment flaps 106, 108 extend along the entire length of the diaper 100, i.e., the length of outer cover 102, to better contain the body exudates.

Figure 3:
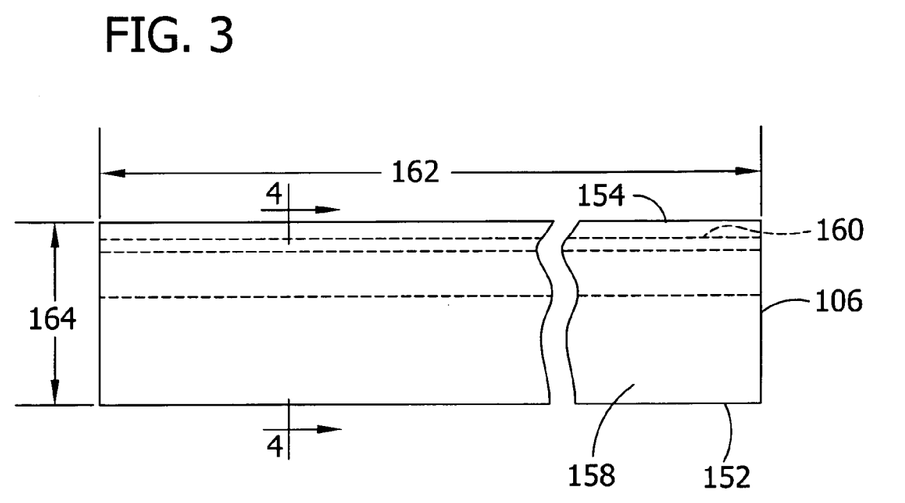
FIG. 3 is a side elevational view of a containment flap according to the present invention.
Figure 4:
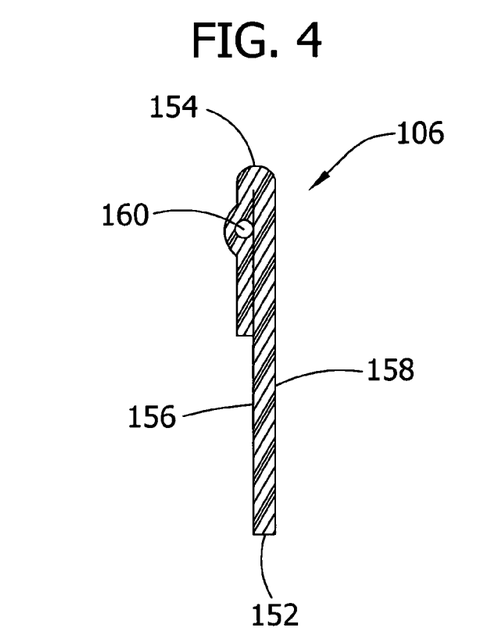
FIG. 4 cross-sectional view taken generally along line 4-4 in FIG. 3.

FIG. 3 illustrates a representative example of one of the containment flaps 106, 108 of the diaper 100 illustrated in FIGS. 1 and 2. The construction of containment flaps 106 and 108 are substantially similar. Accordingly, only the construction of flap 106 will be described in detail. FIG. 4 illustrates a cross-sectional view of the containment flap 106 of FIG. 3 taken generally along lines 4-4. In the different aspects of the present invention, each of the containment flaps 106 is cantilevered from the garment chassis with a proximal edge 152 connected to the garment chassis, a distal, free edge 154, an inner surface 156 and an outer surface 158. The inner surface 156 of each containment flap 106 is the surface of the flap which is configured to face inward towards the lateral or longitudinal centerline 145 or 140 of the diaper 100. While the outer surface 158 of each containment flap 106 is opposite the inner surface 156 and is configured to face outward away from the lateral or longitudinal centerline 145 or 140 of the diaper 100. Each containment flap includes an elastic member 160. In an embodiment, elastic member 160 extends less than the entire length of the flap 106. In an embodiment, elastic member 160 extends a majority of the length of the flap 106. In an embodiment, the ends of the elastic member 160 are fixed to the garment chassis. Each containment flap 106 further defines a length 162 and a width 164.

Two embodiments of flaps of the present invention are illustrated in FIGS. 5 and 6. FIG. 5 illustrates an embodiment of the present invention wherein flaps 106, 108 on one side of the diaper 100, i.e., along one side edge 110, are formed as single layer containment flaps 500. As described herein, single layer containment flaps 500 are the flaps 106, 108 shown on the bottom, right of FIG. 2. In an embodiment, the other adjacent inner flap 106 and outer flap 108 are of the same construction as flap assembly 500. FIG. 6 illustrates an embodiment of the present invention wherein flaps 106, 108 on one side of the diaper 100, i.e., along one side edge 110, are formed as double layer containment flaps 600. As described herein, double layer containment flaps 600 are the flaps 106, 108 shown on the bottom, right of FIG. 2.

The single layer containment flap assembly 500 illustrated in FIG. 5 includes inner containment flap 106 and outer containment flap 108. Both inner containment flap 106 and outer containment flap 108 include elastic members 560 and 561. Elastic members are known in the art and techniques known in the art for incorporating elastics into containment flaps may be advantageously utilized to incorporate elastics into containment flaps according to the present invention. The embodiment illustrated in FIG. 5 comprises containment flaps referred to as single layer flaps. The portion 506 or 508 of the containment flap 106 or 108, respectively, that does not contain the elastic members 560, 561 is a single layer of material. Moreover, in an embodiment, both containment flaps 106, 108 are formed from a same single layer of material. Such a single layer of material is includes an intermediate portion 564 integrally connected to and extending between the flaps 106, 108. An adhesive 570, 571 is positioned at the bottom of each flap 106, 108 to fix the lower portion 152 of each flap to the garment chassis. In an embodiment, the adhesive 570, 571 are elongate beads of adhesive that extend the lengths of the flaps 106, 108. In an embodiment, the adhesive 570, 571 is discontinuous along the lengths of the flaps 106, 108. In an embodiment, the adhesive 570, 571 is only at the ends of the flaps 106, 108. In an embodiment, the adhesive 570, 571 affixes the flaps 106 to the inner, bodyside liner 104.

The dual containment flap assembly 600 illustrated in FIG. 6 includes inner containment flap 606 and outer containment flap 608. Both inner containment flap 606 and outer containment flap 608 are formed of a single piece of material that is folded to create the flaps. Flaps 606, 608 include elastics 561 and 560 as discussed above. However, the material of the flaps 606, 608 does not end at the folded-over portion enclosing the elastics. In this embodiment, a first end 611 and a second end 612 of the flap material are at the bottom portion 664 of the assembly 600. The material extends from first end 611 along the bottom portion 664 and upwardly from lower flap end 152 to upper flap end 154. The material folds over the elastics 560, 561 and inwardly back upon itself to form a double walled, inner flap 606. At the lower flap end 152, the material extends over both the first end 611 and the second end 612 until it reaches the lower flap end 152 of outer flap 608. At this lower flap end 152, the material extends upwardly to outer flap upper end 154. The material folds over elastics 560, 561 and outwardly back onto itself to form a double walled, outer flap 608. The material at the outer flap lower end 152 extends beneath the first layer of bottom portion 664. In an embodiment, the material in bottom layer 664 forms a double wall layer. In an embodiment, the material in a portion of the bottom layer forms a triple wall layer.

Garments of the present invention can be manufactured by utilizing processes known in the art. In preferred embodiments, the containment flap assembly comprising an inner containment flap and an outer containment flap is formed from an integral sheet of containment flap material. The formed containment flap assembly is then attached to the bodyside liner along two lines of attachment. The distance between the containment flaps is measured from the lines of attachment. For example, the distance between an outer containment flap and the closest inner containment flap will be measured from the two corresponding lines of attachment.

The containment flaps 106, 108 may be integral with or formed separate from the garment chassis and joined thereto. The garment chassis includes but is not limited to the bodyside liner 104. In an embodiment, garment chassis includes the absorbent layer 202 and outer cover 102. Suitable methods for forming the containment flaps 106, 108 include heat sealing, sonic bonding, adhesive bonding, and the like. It is generally preferred that the containment flaps 106, 108 be formed separate and attached to the garment chassis. For example, in the embodiment illustrated in FIGS. 1 and 7, it is desirable that the containment flaps 106, 108 be attached to the garment chassis close to the lateral edges (waistband) of the diaper 100, 700 so that the containment flaps extend essentially the entire length of the diaper.

In an embodiment, the containment flaps 106, 108 are integrally formed from the outer cover 102 or bodyside liner 104 of the diaper 100. For example, the bodyside liner 104 may extend from the side edges of the diaper to the absorbent body 202 where the bodyside liner 104 can extend upwardly and be folded over upon itself to form the containment flaps 106, 108.

A wide range of materials are suitable for use as the containment flaps 106, 108 of the present invention. For example, the containment flaps 106, 108 can include a nonwoven material such as a spunbond, meltblown, spun laced or carded polymeric material, a film material such as a polyolefin or polyurethane film, a foam material or combinations thereof. The containment flaps 106, 108 may also include materials described above as being suitable for the outer cover 102 or bodyside liner 104. In a specific embodiment, the containment flaps 106, 108 may be formed from a nonwoven material such as a spunbond or meltblown polyethylene or polypropylene material. Containment flap materials include nonwoven materials, such as thermoplastic polymers, such as polyolefins; bonded carded webs; film materials, such as ethylene vinyl acetate, and ethyl methacrylate films; foam materials, such as polyolefin foams; woven materials, such a woven polypropylene, polyethylene or polyester fabrics; and composites and laminates of the above nonwoven, film, foam, and woven materials.

Many nonwoven materials are formed from hydrophobic materials. Such hydrophobic materials result in nonwovens which are somewhat resistant to the flow of liquids. If it is desired that the containment flaps 106, 108 be generally liquid pervious, such nonwoven materials may be treated with a surfactant to render them generally hydrophilic. Alternatively, if it is desired that the containment flaps 106, 108 be liquid impervious, the containment flaps can include a liquid-impervious film such as a polyolefin film. In a specific embodiment, the containment flaps 106, 108 comprise a spunbond/meltblown/spunbond laminate material having a basis weight of about 30 grams per square meter.

At least a portion of the proximal edge 152 of each containment flap 106, 108 is joined to the garment chassis to maintain a seal between the containment flap and the garment chassis. Desirably, the proximal edge 152 is joined to the garment chassis along the entire length 162 or width 164 of the containment flap 106, 108 for improved containment of body exudates and reduced leakage. For example, as representatively illustrated in FIGS. 1 and 7, the proximal edge 152 of each containment flap 106, 108 may be joined to the bodyside liner 104 at least in the intermediate, crotch portion 126 and desirably along the entire length of the containment flap 106, 108. That is, the flap is cantilevered from the chassis. If the containment flap 106, 108 is located in a waist region, then at least a portion of the proximal edge 152 of each containment flap 106, 108 is joined to the bodyside liner 104 adjacent the end edge of the diaper and desirably along the entire width of the containment flap 106, 108.

At least a portion of the distal edge 154 of each containment flap 106, 108 is not attached to the garment chassis such that the containment flap 106, 108 provides a barrier to the lateral flow of body exudates. For example, the distal edge 154 of each containment flap 106, 108 may be joined to the bodyside liner 104 in at least a portion of the front waist portion 122 and rear waist portion 124 and remain unjoined to the bodyside liner 104 in at least a portion of the intermediate section 126. In such a configuration, the distal edge 154 of each containment flap is configured to position itself in a spaced relation away from the garment chassis toward a generally upright and approximately perpendicular configuration in at least the intermediate section 126. Alternatively, the distal edge 154 of each containment flap may be joined to the bodyside liner 104 adjacent the side edges of the diaper and remain unjoined to the bodyside liner 104 in at least a portion of the diaper 20 between its side edges. In such a configuration, the distal edge 154 of each containment flap is configured to position itself in a spaced relation away from the garment chassis toward a generally upright and approximately perpendicular configuration in between the side edges of the diaper.

To achieve such a spaced away, upright configuration, each containment flap 106, 108 includes at least one elastic member 160 or 560 along at least a portion of the distal edge 154 of the containment flaps and, more desirably, along the entire distal edge of the containment flap. The elastic member 160 or 560 is secured to the containment flap 106, 108 in an elastically contractible condition so that in a normal under strain configuration, the elastic member 160 or 560 effectively contracts against the containment flap. For example, the elastic member 160 or 560 may be elongated and secured to the containment flap 550 while the flap is in an uncontracted condition. The elastic members 160 or 560 are illustrated in their uncontracted, stretched condition for the purpose of clarity in FIGS. 3 and 5. As a result, the distal edge 154 of each containment flap tends to contract or gather and position itself in a spaced relation away from the garment chassis and, in particular, away from the bodyside liner 104 toward a generally upright and approximately perpendicular configuration.

Each containment flap 106, 108 may include any number of individual elastic members which provide the desired spaced away configuration. In the illustrated embodiments, each containment flap 106, 108 includes an elastic member 160 which is in the form of a single elastomeric strand. Alternatively, each containment flap may include from about 2 to about 10 elastomeric strands, e.g., 560, 561. Multiple elastomeric strands may be configured in a laterally spaced, generally parallel arrangement. Suitably, the elastic member 160, 560 or 561 is configured parallel to the distal edge 154 and is located within about 0.5 centimeters of the distal edge 154.

The elastic member 160, 560 or 561 suitably comprises any elastomeric material capable of being elongated at least about 50 percent, desirably about 350 percent, and capable of recovering to within at least about 250 percent, and desirably about 150 percent of its original length after being elongated about 300 percent. In one specific embodiment, the elastic member 160, 560 or 561 can, for example, be composed of a spandex elastomeric strand such as, for example, a 470 decitex LYCRA thread commercially available from E. I. DuPont de Nemours and Co. Alternatively, the elastic member 160, 560 or 561 can be composed of a thermoplastic elastomer or a natural or synthetic rubber commercially available from J.P.S. Elastomerics Corp. The elastic member 160, 560 or 561 can also be composed of a heat activatable elastic material such as PEBAX, commercially available from Atochem, Inc., which can be activated with heat treatment after the elastic member 160, 560 or 561 is secured to the containment flap. The elastic member can be attached to the containment flap by any method known to those skilled in the art such as thermal bonding, adhesive bonding, ultrasonic bonding or the like.

In another aspect, the inner and outer flaps 106, 108 of the absorbent garment 100, 700 of the present invention may also define an elasticized length. As used herein, the term "elasticized length" means the total length along the flap 106, 108 that is under tension due to the elastic components 160, 560, 561 within the flap. The elasticized length may therefore be one continuous length along the flap 106, 108 or it may be the sum of discrete segments along the flap length which may each be under tension due to the elastic components 160, 560, 561 within the flap. The inner flap 106 and outer flap 108 on either side of the absorbent garment 100, 700 may have substantially similar elasticized lengths. For example, the inner flap 106 and outer flap 108 may each have an elasticized length of about 100% of the overall garment length. In another aspect, the inner flap 106 and outer flap 108 may each have elasticized lengths of from about 50% to about 100% of the diaper (e.g., chassis) length. In yet another aspect, the elasticized length of the inner flap 106 and outer flap 108 may be of from about 70% to about 80% of the diaper length.

Alternatively, the inner flap 106 and outer flap 108 may be configured to have different elasticized lengths. For example, the inner flap 106 may have a longer elasticized length than the outer flap 108. Desirably, the outer flap 108 defines a substantially longer elasticized length than the inner flap 106. Such an arrangement would advantageously provide improved fit and containment benefits. Specifically, the longer elasticized length of the outer flap 108 would allow the outer flap 108 to better follow the contour of the wearer's leg in use, while the shorter elasticized length of the inner flap 106 would better provide a void volume "bucket" in the crotch region 126 of the garment 100, 700 for better fluid containment. In a particular aspect, the outer flap 108 would define an elasticized length of from about 50% to about 100% of the garment length while the inner flap 106 defines an elasticized length that is less than that of the outer flap 108, of from about 20% to about 80% of the garment length. More particularly, the outer flap 108 would define an elasticized length of from about 70% to about 80% of the garment length while the inner flap 106 defines an elasticized length of from about 40% to about 60% of the garment length. In an advantageous aspect, the outer flap 108 would define an elasticized length of about 75% of the garment length while the inner flap 106 would define an elasticized length of 50% of the total garment length.

The elasticized length of the inner flap 106 and outer flap 108 may be provided in any number of ways, as appreciated by one of skill in the art. For example, the elastic components may be provided within the inner and outer flaps over only a particular portion of the flap. Alternatively, the elastic components may be located substantially continuously over the length of the flap, yet configured to be in a relaxed state in certain portions of the containment flap. Specifically, the elastic components within the flap may not be actively attached to the containment flap material in portions of the flap. As such, the containment flap would not exhibit tension in those portions of the flap where the elastic component was not attached.

The length 162 and width 164 of each containment flap 106, 108 can vary depending on the type and size of the absorbent article to which it will be attached and the orientation of the containment flap on the garment or diaper 100, 700. In a specific embodiment wherein the containment flaps are disposed along the side edges of the diaper as illustrated in FIGS. 3 and 4, each containment flap has an overall width 164 of at least about 1 centimeter and desirably from about 2 to about 3 centimeters and an overall length 162 of at least about 30 percent and desirably at least about 50 percent of the entire length of the diaper. In a particular embodiment, the containment flap will extend substantially the entire length of the diaper for improved containment.

The dual containment flaps 106, 108 of the present invention may be configured in any number of ways. For example, each outer containment flap 108 may be directed toward the longitudinal side edges 110 of the diaper 100, 700. In an embodiment, the outer flaps 108 may be directed toward the longitudinal centerline of the diaper. In an embodiment, each inner containment flap 106 is directed toward the longitudinal side edges of the diaper 100, 700. In an embodiment, the inner flaps 106 are directed toward the longitudinal centerline of the diaper. In an embodiment, both the inner and outer flaps 106, 108 are directed toward the longitudinal side edges of the diaper. In an embodiment, at least one of the flaps 106, 108 are curvilinear. As shown in FIGS. 2-7, the pairs of containment flaps 106, 108 on each side of the diaper are substantially linear and parallel to each other. In an embodiment, all of the containment flaps 106, 108 are parallel with the side edges of the diaper. In an embodiment, all of the containment flaps 106, 108 are parallel with the longitudinal center line of the diaper. In an embodiment, the containment flaps 106, 108 follow the side edges 110 of the diaper. In an embodiment, the containment flaps are equal distance from each other. In an embodiment, inner containment flaps 106 are equal distant from the side edge 110 of the diaper. In an embodiment, outer containment flaps 108 are equal distant from the side edge 110 of the diaper. It will be appreciated that the side edges 110 may include a curved portion.

Generally, the distance between the two inner containment flaps 106 will be at least about 50 mm. Larger distances between the two inner containment flaps 106 are typically used when it is anticipated that more area or volume is needed to provide an adequate void volume to entrap discharged waste. In an embodiment, the inner containment flaps 106 are less than about 160 mm apart. In an embodiment, the inner containment flaps are less than about 140 mm apart. In an embodiment, the inner containment flaps are less than about 120 mm apart. In an embodiment, the inner containment flaps 106 are greater than about 100 mm apart. In an embodiment, the inner containment flaps are less than about 110 mm apart. In an embodiment, the inner containment flaps are less than about 120 mm apart. In a preferred embodiment the two inner containment flaps 106 are positioned about 120 mm apart. It will be appreciated that other distances between the two inner containment flaps 106 are within the scope of the present invention.

Generally, each outer containment flap 108 is positioned parallel or at a constant distance to the closest inner containment flap 106 and spaced therefrom in a range of about zero mm to about 30 mm. In an embodiment, each outer containment flap is positioned parallel to the closest inner flap and is positioned no more than about 25 mm from the closest inner containment flap. Preferably, each outer containment flap is positioned no more than about 20 mm from the closest inner containment flap. In one preferred embodiment, each outer containment flap is positioned about 12 mm from the closest inner containment flap. In one preferred embodiment, each outer containment flap 108 is spaced about 5 mm from the adjacent inner containment flap 106.

The distance from the outer containment flap 108 and the side edge 110 of the garment may vary along the length of the outer containment flap as the outer containment flap may not run parallel to the outer edge of the garment (depending on the shape of the garment). The outer containment flaps typically are closest to the edge of the garment along the leg cut out portion 110 of the garment as shown in FIG. 2. Generally, the outer containment flaps will be no closer than about 5 mm from the edge of the garment at any point along the length of the outer containment flaps. This provides a manufacturing clearance so that the containment flap 108 is not damaged when the leg holes are created in the diaper.

It has been discovered that garments in accordance with the present invention exhibit reduced leakage when the elastic tensions of the inner and outer containment flaps 106, 108 are substantially equal. As used in reference to the elastic tensions of the inner and outer containment flaps 106, 108, "substantially equal" means that the elastic tensions of the flaps are within at least about 10 percent of each other, and more desirably within about 5 percent of each other. Thus, the elastic tensions of both the inner containment flaps and the outer containment flaps 106, 108 in garments of the present invention are adjusted to be substantially equal. The elastic tensions of the flaps 106, 108 can be adjusted utilizing methods of manufacture known in the art. Generally, higher elastic tensions are utilized when the intended wearer is an older, larger and generally more active child. For example, diapers made to be used on such children will have containment flaps having higher elastic tensions. Similarly, containment flaps having lower elastic tensions can be utilized in diapers intended to be used on smaller children that are typically more sensitive to flap tensions and red marking.

For the purpose of further describing the present invention, the elastic tension of the containment flaps 106, 108 of diapers constructed in accordance with the present invention is determined by the following test method, which is otherwise referred to herein as an Elastic Tension Test. Each diaper to be tested is hung from a conventional lightbox or other suitable device in an unfolded, vertical orientation with one end (e.g., the back end) of the diaper up and the bodyside liner of the diaper facing laterally outward away from the lightbox. The lightbox includes a pair of fixed upper clamps spaced approximately 5.5 inches apart at their centerlines (e.g., spaced in accordance with the approximate spacing between the containment flaps on the opposite sides of the diaper). The waistband at the back end of the diaper is generally fully stretched (e.g., to eliminate gathers in or otherwise straighten the waistband) and the clamps are clamped to the waistband without clamping any of the absorbent core therein. The operator then gently runs his or her fingers down the sides of the containment flaps to straighten and extend the diaper.

The waistband at the front (i.e., lower) end of the diaper is then generally fully stretched (i.e., to eliminate gathers in or otherwise straighten the waistband) and a clamp weight is secured to the waistband at the front end of the diaper so that the diaper hangs freely from the upper clamps in a longitudinally elongated configuration. The clamp weight is approximately 1,000 grams total mass and includes a pair of clamps spaced approximately 5.5 inches apart at their centerlines (e.g., spaced approximately the same as the clamps attached to the back end of the diaper) for attaching the clamp weight to the front end of the diaper.

With the diaper in this longitudinally elongated configuration, a pair of markings is made on each containment flap generally where the elastics are attached to the flap. More particularly, the markings on each containment flap are spaced longitudinally from each other a distance of about 178 mm and are equidistant from the longitudinal center of the flap. The clamp weight is then removed from the diaper and the diaper is removed from the lightbox. Each containment flap is cut from the diaper by first cutting the containment flap inward from the free (i.e., distal) edge of the flap to the secured edge of the flap at longitudinally spaced locations which are approximately 0.5 inches (12.85 mm) beyond each of the markings (e.g., toward the nearest end of the diaper) made on the flap, and then cutting lengthwise generally adjacent the bead of adhesive which secures the secured edge of the flap to the liner.

Each test specimen (e.g., the marked and cut portion of each containment flap) is then secured in a testing device by a generally fixed upper clip and a generally moveable lower clip, both of which are constructed to inhibit the specimen against slipping or becoming damaged upon tensioning the specimen. More particularly, the specimen is first secured at one end by the upper clip, with the specimen marking near the one end being aligned with the leading edge (e.g., the lowermost edge) of the upper clip so that the specimen hangs freely from the upper clip in a generally relaxed (e.g., unstretched) condition. The weight of the specimen is tared and then the other end of the specimen is secured by the lower clip, with the marking near this end of the specimen being aligned with the leading edge (e.g., uppermost edge) of the lower clip. The lower clip is then moved longitudinally away from the upper clip until the specimen is elongated longitudinally to about 90% of the previously achieved longitudinally elongated configuration (e.g., to a configuration in which the spacing between the markings on the specimen is about 160 mm, which is 90% of 178 mm) of the diaper. The specimen is maintained in this condition for about thirty seconds. The elastic tension is then measured and recorded using a suitable force gauge. The containment flaps 106, 108 of at least five like diapers are tested using the identical procedure and the results are averaged to determine the elastic tension in the flaps.

As an example, in one embodiment the elastic tension in the inner and outer containment flaps 106, 108 as determined by the Elastic Tension Test is greater than about 40 grams. In another embodiment, the elastic tension is greater than about 45 grams. In another embodiment, the elastic tension is greater than about 50 grams. In yet another embodiment, the elastic tension is greater than about 55 grams. In still another embodiment, the elastic tension is greater than about 60 grams. In another embodiment, the elastic tension is greater than about 65 grams and in still another embodiment, the elastic tension is greater than about 70 grams. In another embodiment, the elastic tension is less than about 55 grams. In another embodiment, the elastic tension is less than about 60 grams. In another embodiment, the elastic tension is less than about 65 grams. In another embodiment, the elastic tension is less than about 70 grams, and in yet another embodiment, the elastic tension is less than about 80 grams. In one embodiment, the elastic tension is desirably in the range of about 40 grams to about 80 grams, more desirably in the range of about 50 grams to about 70 grams, and most desirably about 60 grams. It has been found that elastic tensions less than 40 grams do not provide adequate gasketing by the dual containment flaps 106, 108 to prevent leakage of bodily exudates. It has also been found that elastic tensions greater than 80 grams marks the skin to such an extent that skin marking becomes a concern.

It has also been discovered that garments according to the present invention exhibit reduced leakage if the height of both the inner containment flaps 106 and the outer containment flaps 108 is substantially equal. As used in reference to the height of the inner and outer containment flaps 106, 108, "substantially equal" means that the heights of the flaps are within at least about 10 percent of each other and more desirably within about 5 percent of each other. For the purpose of further describing the present invention, the height of the containment flaps 106, 108 of diapers constructed in accordance with the present invention is determined by the following method.

Each diaper to be measured is hung from a conventional lightbox or other suitable device in an unfolded, vertical orientation with one end (e.g., the back end) of the diaper up and the bodyside liner and flaps facing laterally outward away from the lightbox. The lightbox includes a pair of fixed upper clamps spaced approximately 5.5 inches apart at their centerlines (e.g., in accordance with the approximate spacing between the containment flaps on the opposite sides of the diaper). The waistband at the back end of the diaper is generally fully stretched (e.g., to eliminate gathers in or otherwise straighten the waistband) and the clamps are clamped to the waistband without clamping any of the absorbent core therein. The operator then gently runs his or her fingers down the sides of the containment flaps to straighten and extend the diaper.

The waistband at the front (i.e., lower) end of the diaper is then generally fully stretched (i.e., to eliminate gathers in or otherwise straighten the waistband) and a clamp weight is secured to the waistband at the front end of the diaper so that the diaper hangs freely from the upper clamps in a longitudinally elongated configuration. The clamp weight is approximately 1,000 grams total mass and includes a pair of clamps spaced approximately 5.5 inches apart at their centerlines (e.g., spaced approximately the same as the clamps attached to the back end of the diaper) for attaching the clamp weight to the front end of the diaper. The height of each containment flap is then measured, to the nearest millimeter, at the longitudinal center of the containment flap. The height is measured from the adhesive that attaches the flap to the bodyside liner to the distal edge of the flap.

Generally, the height of containment flaps 106, 108 according to the present invention is in the range of about 22 mm to about 40 mm. In an embodiment, the height of the flaps 106, 108 is at least about 27 mm. In an embodiment, the height of the containment flaps 106, 108 is at least 30 mm. In an embodiment, the height of the containment flaps 106, 108 is at least 35 mm. In an embodiment, the height of the containment flaps is less than 35 mm. In an embodiment, the height of the containment flaps is less than 30 mm. In one preferred embodiment, the height of both the inner containment flaps and the outer containment flaps is about 27 mm. In another preferred embodiment, the height of the flaps is 27.0 mm. In an embodiment, the heights of the flaps are not equal.

Figure 7:
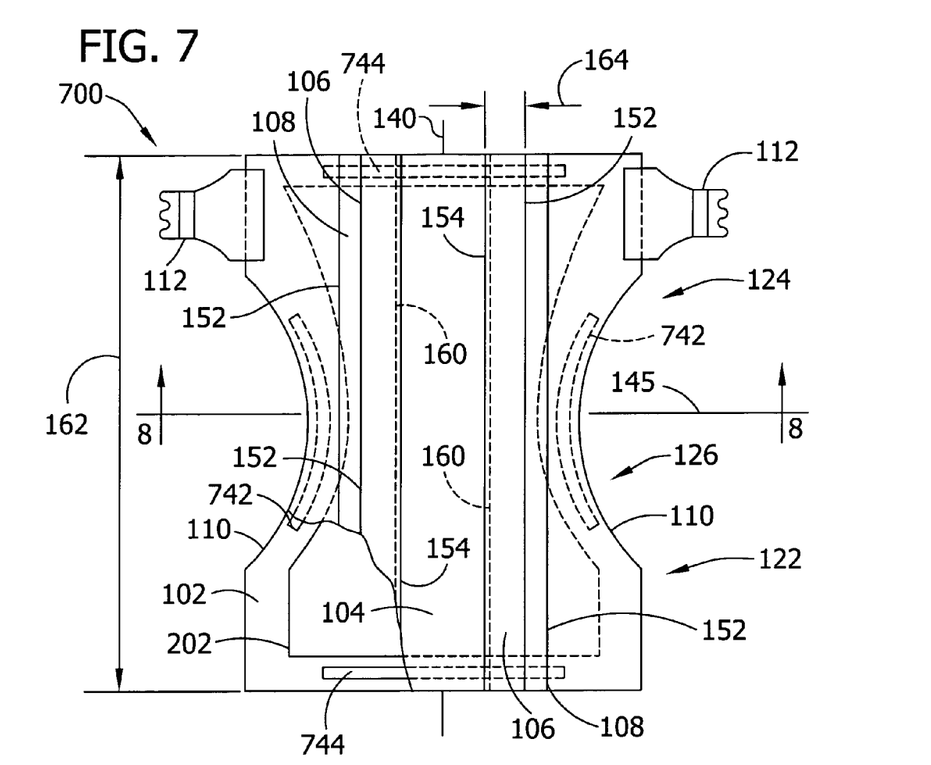
FIG. 7 is a plan view of a diaper in a flat state showing the side of the diaper that faces the wearer when worn and with a bodyside liner partially broken away to reveal internal construction.
Figure 8:
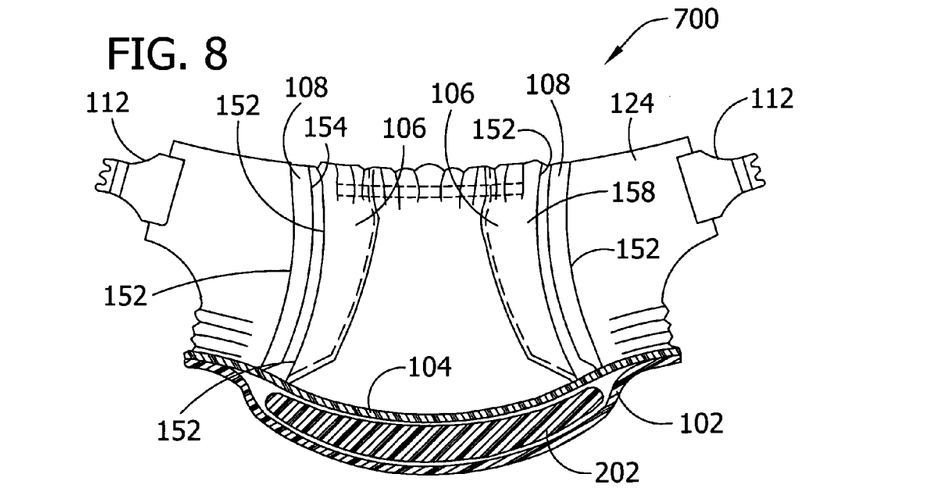
FIG. 8 is a cross-sectional view taken along line 8-8 in FIG. 7.

FIGS. 7 and 8 show another embodiment of a diaper according to the present invention. Like numbers are used to designate similar elements. Accordingly, description of these similar elements is not repeated here. To provide improved fit and to help reduce leakage of body exudates from the diaper 700, the side margins and end margins of the diaper may be elasticized with suitable elastic members, such as leg elastic members 742 and waist elastic members 744. For example, the leg elastic members 742 may include single or multiple strands of elastic or elastomeric composites which are constructed to operably gather and shirr the side margins of the diaper 700 to provide elasticized leg bands which can closely fit around the legs of the wearer to reduce leakage and provide improved comfort and appearance. Similarly, the waist elastic members 744 can be employed to elasticize the end margins of the diaper 700 to provide elasticized waistbands. The waist elastics are configured to operably gather and shirr the waistband sections to provide a resilient, comfortably close fit around the waist of the wearer.

The elastic members 742 and 744 are secured to the diaper 700 in an elastically contractible condition so that in a normal under strain configuration, the elastic members effectively contract against the diaper 700. For example, the elastic members 742 and 744 may be elongated and secured to the diaper 700 while the diaper is in an uncontracted condition. In FIGS. 7 and 8, the elastic members 742 and 744 are illustrated in their uncontracted, stretched condition for the purpose of clarity. Alternatively, the diaper 700 may include a pair of separate, elasticized and gathered leg gussets (not shown) which are attached to the diaper along the side margins in at least the intermediate section 126 of the diaper 700 to provide elasticized leg cuffs. Such leg gussets may be configured to extend beyond and bridge across the respective concave portion of the side margins of the diaper 700.

CONCLUSION

The various embodiments of the present invention advantageously provide an absorbent garment having improved containment flaps. In particular, the present invention provides dual containment flaps for absorbent garments. Such flaps have substantially equal elastic tension for improved containment of bodily exudates. The dual containment flaps according to an embodiment of the present invention are also substantially similar in height for improved performance, such as containment. During use, exudates that pass over or leak past the distal edge of the first containment flap are contained by the second containment flap. Consequently, the dual containment flaps reduce the amount or level of leakage from the absorbent garment.

Moreover, the elastic tension of the dual containment flaps 106, 108 creates a secure seal and avoids skin irritation and skin marking. The dual containment flaps 106, 108 are stacked so that an outer containment flap is over the inner containment flap. The inner containment flap 106 forms the receptacle to catch and retain the exudates while the outer containment flap reinforces the leg gasketing for a comfortable fit and leakage protection. Such a double containment flap structure is especially advantageous in narrow crotch garments, which fit better between the legs but are less absorbent in the crotch area due to less material in the crotch. The dual containment flaps 106, 108 provide improved gasketing to contain exudates even with narrow, less absorbent crotch garments.

The preceding disclosure describes the present invention in the context of a disposable diaper that is adapted to be worn about the lower torso. It is apparent that the present invention is also suitable for use with other articles, such as but not limited to feminine care or hygiene pads, incontinence garments, training pants, and the like. Typically, garments according to the teachings of the present invention are disposable, intended for limited use, and not intended to be laundered or otherwise cleaned for additional use.

While the present invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:
1. An absorbent garment comprising:
a garment chassis having a length;

a pair of outer containment flaps extending generally lengthwise on the garment chassis, each outer containment flap comprising a flap material and at least one elastic member secured to at least a portion of the flap material, each outer containment flap having an elasticized length in the range of about 60 percent to about 100 percent of the length of the chassis, each outer containment flap also having an elastic tension as determined by an Elastic Tension Test; and a pair of inner containment flaps extending generally lengthwise on the garment chassis, each of the inner containment flaps being constructed at least in part of a liquid impervious material, each inner containment flap comprising a flap material and at least one elastic member secured to at least a portion of the flap material, each of said inner containment flaps having an elasticized length less than the elasticized length of each of the outer containment flaps, each inner containment flap also having an elastic tension as determined by the Elastic Tension Test which is substantially equal to the elastic tension of each outer containment flap.

2. The absorbent garment set forth in claim 1 wherein the elastic tension of each of the inner and outer containment flaps as determined by the Elastic Tension Test is in the range of about 40 grams to about 80 grams.

3. The absorbent garment set forth in claim 2 wherein the elastic tension of each of the inner and outer containment flaps as determined by the Elastic Tension Test is in the range of about 50 grams to about 70 grams.

4. The absorbent garment set forth in claim 3 wherein the elastic tension of each of the inner and outer containment flaps as determined by the Elastic Tension Test is about 60 grams.

5. The absorbent garment set forth in claim 1 wherein the garment chassis comprises an outer cover, a bodyside liner, and an absorbent core disposed intermediate the outer cover and the bodyside liner.

6. The absorbent garment set forth in claim 5 wherein the inner and outer containment flaps are attached to the bodyside liner.

7. The absorbent garment set forth in claim 1 wherein each of said inner containment flaps is adjacent a respective one of said outer containment flaps, each pair of adjacent inner and outer containment flaps being formed at least in part from a continuous sheet.

8. The absorbent garment set forth in claim 7 wherein said continuous sheet is a single ply sheet.

9. The absorbent garment set forth in claim 7 wherein each pair of adjacent inner and outer containment flaps has a double ply portion.

10. The absorbent garment set forth in claim 9 wherein said double ply portion is adjacent the garment chassis.

11. The absorbent garment set forth in claim 1 wherein each of the inner and outer containment flaps comprises a spunbond/meltblown/spunbond laminate.

12. The absorbent garment set forth in claim 1 wherein the height of at least one of the inner and outer containment flaps is about 27 mm.

13. The absorbent garment set forth in claim 1 wherein the chassis has opposite side edges extending longitudinally of the chassis, the outer containment flaps being positioned approximately 5 mm inward from the respective side edges of the chassis.

14. The absorbent garment set forth in claim 7 wherein each inner containment flap is spaced a constant distance from an adjacent one of the outer containment flaps.

15. The absorbent garment set forth in claim 14 wherein the constant distance is less than or equal to about 30 mm.

16. The absorbent garment set forth in claim 14 wherein the constant distance is less than or equal to about 25 mm.

17. The absorbent garment set forth in claim 14 wherein the constant distance is less than or equal to about 20 mm.

18. The absorbent garment set forth in claim 14 wherein the constant distance is less than or equal to about 12 mm.

19. The absorbent garment set forth in claim 14 wherein the constant distance is less than or equal to about 5 mm.

20. The absorbent garment set forth in claim 1 wherein the inner containment flaps have a height which is within at least 10 percent of a height of the outer containment flaps.

21. The absorbent garment set forth in claim 1 wherein the height of the inner and outer containment flaps is in the range of about 22 mm to about 40 mm.

22. The absorbent garment set forth in claim 21 wherein the height of the inner and outer containment flaps is in the range of about 27 mm to about 40 mm.

23. The absorbent garment set forth in claim 1 wherein each outer containment flap has an elasticized length in the range of about 70 percent to about 80 percent of the length of the chassis.

* * * * *